US008400290B2

(12) United States Patent
Baker, Jr.

(10) Patent No.: US 8,400,290 B2
(45) Date of Patent: Mar. 19, 2013

(54) NUISANCE ALARM REDUCTION METHOD FOR THERAPEUTIC PARAMETERS

(75) Inventor: Clark R. Baker, Jr., Newman, CA (US)

(73) Assignee: Covidien LP, Mansfield, MA (US)

( * ) Notice: Subject to any disclaimer, the term of this patent is extended or adjusted under 35 U.S.C. 154(b) by 574 days.

(21) Appl. No.: 12/689,900

(22) Filed: Jan. 19, 2010

(65) Prior Publication Data

US 2011/0175728 A1  Jul. 21, 2011

(51) Int. Cl.
*G08B 23/00* (2006.01)

(52) U.S. Cl. ........ 340/500; 340/611; 340/614; 340/626; 340/679; 128/202.16; 128/204.18; 128/205.25; 600/300; 600/301; 600/323; 600/324; 600/365

(58) Field of Classification Search .................. 340/500, 340/611, 614, 626, 679; 128/202.16, 204.18, 128/205.25; 600/300, 301, 323, 324, 365

See application file for complete search history.

(56) References Cited

U.S. PATENT DOCUMENTS

| | | |
|---|---|---|
| 4,752,089 A | 6/1988 | Carter |
| 4,921,642 A | 5/1990 | LaTorraca |
| 4,954,799 A | 9/1990 | Kumar |
| 5,057,822 A | 10/1991 | Hoffman |
| 5,072,737 A | 12/1991 | Goulding |
| 5,150,291 A | 9/1992 | Cummings et al. |
| 5,161,525 A | 11/1992 | Kimm et al. |
| 5,237,987 A | 8/1993 | Anderson et al. |
| 5,271,389 A | 12/1993 | Isaza et al. |
| 5,279,549 A | 1/1994 | Ranford |
| 5,299,568 A | 4/1994 | Forare et al. |
| 5,301,921 A | 4/1994 | Kumar |
| 5,319,540 A | 6/1994 | Isaza et al. |
| 5,325,861 A | 7/1994 | Goulding |
| 5,333,606 A | 8/1994 | Schneider et al. |
| 5,339,807 A | 8/1994 | Carter |
| 5,343,857 A | 9/1994 | Schneider et al. |
| 5,351,522 A | 10/1994 | Lura |
| 5,357,946 A | 10/1994 | Kee et al. |
| 5,368,019 A | 11/1994 | LaTorraca |
| 5,383,449 A | 1/1995 | Forare et al. |
| 5,385,142 A | 1/1995 | Brady et al. |
| 5,390,666 A | 2/1995 | Kimm et al. |
| 5,401,135 A | 3/1995 | Stoen et al. |
| 5,402,796 A | 4/1995 | Packer et al. |
| 5,407,174 A | 4/1995 | Kumar |
| 5,413,110 A | 5/1995 | Cummings et al. |
| 5,438,980 A | 8/1995 | Phillips |
| 5,443,075 A | 8/1995 | Holscher |
| 5,513,631 A | 5/1996 | McWilliams |
| 5,517,983 A | 5/1996 | Deighan et al. |

(Continued)

OTHER PUBLICATIONS

7200 Series Ventilator, Options, and Accessories: Operator's Manual. Nellcor Puritan Bennett, Part No. 22300 A, Sep. 1990.

(Continued)

*Primary Examiner* — Tai T Nguyen

(57) ABSTRACT

This disclosure describes systems and methods for reducing nuisance alarms associated with monitoring non-physiological parameters in a ventilatory system. Non-physiological parameters may include, but are not limited to, parameters that are internally monitored by the ventilator based on preconfigured ranges dictated by the manufacturer, by an applicable protocol, or by the clinician. Embodiments described herein seek to mitigate nuisance alarms by basing alarm conditions, at least in part, on an integral threshold such that an alarm is not generated when a monitored parameter briefly falls outside an acceptable range by a slight degree, but such that an alarm is generated when a monitored parameter falls outside an acceptable range by a more significant magnitude and/or duration.

11 Claims, 6 Drawing Sheets

U.S. PATENT DOCUMENTS

| | | |
|---|---|---|
| 5,520,071 A | 5/1996 | Jones |
| 5,524,615 A | 6/1996 | Power |
| 5,531,221 A | 7/1996 | Power |
| 5,542,415 A | 8/1996 | Brody |
| 5,544,674 A | 8/1996 | Kelly |
| 5,549,106 A | 8/1996 | Gruenke et al. |
| 5,596,984 A | 1/1997 | O'Mahoney et al. |
| 5,630,411 A | 5/1997 | Holscher |
| 5,632,270 A | 5/1997 | O'Mahoney et al. |
| 5,645,048 A | 7/1997 | Brodsky et al. |
| 5,660,171 A | 8/1997 | Kimm et al. |
| 5,664,560 A | 9/1997 | Merrick et al. |
| 5,664,562 A | 9/1997 | Bourdon |
| 5,671,767 A | 9/1997 | Kelly |
| 5,672,041 A | 9/1997 | Ringdahl et al. |
| 5,673,689 A | 10/1997 | Power |
| 5,715,812 A | 2/1998 | Deighan et al. |
| 5,762,480 A | 6/1998 | Adahan |
| 5,771,884 A | 6/1998 | Yarnall et al. |
| 5,791,339 A | 8/1998 | Winter |
| 5,794,986 A | 8/1998 | Gansel et al. |
| 5,813,399 A | 9/1998 | Isaza et al. |
| 5,826,575 A | 10/1998 | Lall |
| 5,829,441 A | 11/1998 | Kidd et al. |
| 5,864,938 A | 2/1999 | Gansel et al. |
| 5,865,168 A | 2/1999 | Isaza |
| 5,881,717 A | 3/1999 | Isaza |
| 5,881,723 A | 3/1999 | Wallace et al. |
| 5,884,623 A | 3/1999 | Winter |
| 5,909,731 A | 6/1999 | O'Mahony et al. |
| 5,915,379 A | 6/1999 | Wallace et al. |
| 5,915,380 A | 6/1999 | Wallace et al. |
| 5,915,382 A | 6/1999 | Power |
| 5,918,597 A | 7/1999 | Jones et al. |
| 5,921,238 A | 7/1999 | Bourdon |
| 5,934,274 A | 8/1999 | Merrick et al. |
| 6,024,089 A | 2/2000 | Wallace et al. |
| 6,041,780 A | 3/2000 | Richard et al. |
| 6,047,860 A | 4/2000 | Sanders |
| 6,076,523 A | 6/2000 | Jones et al. |
| 6,116,240 A | 9/2000 | Merrick et al. |
| 6,116,464 A | 9/2000 | Sanders |
| 6,123,073 A | 9/2000 | Schlawin et al. |
| 6,135,106 A | 10/2000 | Dirks et al. |
| 6,142,150 A | 11/2000 | O'Mahoney et al. |
| 6,161,539 A | 12/2000 | Winter |
| 6,220,245 B1 | 4/2001 | Takabayashi et al. |
| 6,269,812 B1 | 8/2001 | Wallace et al. |
| 6,273,444 B1 | 8/2001 | Power |
| 6,283,119 B1 | 9/2001 | Bourdon |
| 6,305,373 B1 | 10/2001 | Wallace et al. |
| 6,321,748 B1 | 11/2001 | O'Mahoney |
| 6,325,785 B1 | 12/2001 | Babkes et al. |
| 6,357,438 B1 | 3/2002 | Hansen |
| 6,360,745 B1 | 3/2002 | Wallace et al. |
| 6,369,838 B1 | 4/2002 | Wallace et al. |
| 6,412,483 B1 | 7/2002 | Jones et al. |
| 6,439,229 B1 | 8/2002 | Du et al. |
| 6,467,478 B1 | 10/2002 | Merrick et al. |
| 6,546,930 B1 | 4/2003 | Emerson et al. |
| 6,553,991 B1 | 4/2003 | Isaza |
| 6,557,553 B1 | 5/2003 | Borrello |
| 6,571,795 B2 | 6/2003 | Bourdon |
| 6,622,726 B1 | 9/2003 | Du |
| 6,644,310 B1 | 11/2003 | Delache et al. |
| 6,668,824 B1 | 12/2003 | Isaza et al. |
| 6,675,801 B2 | 1/2004 | Wallace et al. |
| 6,718,974 B1 | 4/2004 | Moberg |
| 6,725,447 B1 | 4/2004 | Gilman et al. |
| 6,739,337 B2 | 5/2004 | Isaza |
| 6,761,167 B1 | 7/2004 | Nadjafizadeh et al. |
| 6,761,168 B1 | 7/2004 | Nadjafizadeh et al. |
| 6,814,074 B1 | 11/2004 | Nadjafizadeh et al. |
| 6,866,040 B1 | 3/2005 | Bourdon |
| 6,960,854 B2 | 11/2005 | Nadjafizadeh et al. |
| 7,036,504 B2 | 5/2006 | Wallace et al. |
| 7,077,131 B2 | 7/2006 | Hansen |
| RE39,225 E | 8/2006 | Isaza et al. |
| 7,117,438 B2 | 10/2006 | Wallace et al. |
| 7,270,126 B2 | 9/2007 | Wallace et al. |
| 7,369,757 B2 | 5/2008 | Farbarik |
| 7,370,650 B2 | 5/2008 | Nadjafizadeh et al. |
| 7,428,902 B2 | 9/2008 | Du et al. |
| 7,460,959 B2 | 12/2008 | Jafari |
| 7,487,773 B2 | 2/2009 | Li |
| 7,654,802 B2 | 2/2010 | Crawford, Jr. et al. |
| 7,694,677 B2 | 4/2010 | Tang |
| 7,717,113 B2 | 5/2010 | Andrieux |
| D618,356 S | 6/2010 | Ross |
| 7,784,461 B2 | 8/2010 | Figueiredo et al. |
| 7,823,588 B2 | 11/2010 | Hansen |
| 7,855,716 B2 | 12/2010 | McCreary et al. |
| D632,796 S | 2/2011 | Ross et al. |
| D632,797 S | 2/2011 | Ross et al. |
| 7,891,354 B2 | 2/2011 | Farbarik |
| 7,893,560 B2 | 2/2011 | Carter |
| D638,852 S | 5/2011 | Skidmore et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 8,001,967 B2 | 8/2011 | Wallace et al. |
| 8,021,310 B2 | 9/2011 | Sanborn et al. |
| D649,157 S | 11/2011 | Skidmore et al. |
| 8,113,062 B2 | 2/2012 | Graboi et al. |
| 8,181,648 B2 | 5/2012 | Perine et al. |
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 2005/0039748 A1 | 2/2005 | Andrieux |
| 2005/0139212 A1 | 6/2005 | Bourdon |
| 2007/0017515 A1 | 1/2007 | Wallace et al. |
| 2007/0077200 A1 | 4/2007 | Baker |
| 2007/0227537 A1 | 10/2007 | Bemister et al. |
| 2007/0284361 A1 | 12/2007 | Nadjafizadeh et al. |
| 2008/0053441 A1 | 3/2008 | Gottlib et al. |
| 2008/0072896 A1 | 3/2008 | Setzer et al. |
| 2008/0072902 A1 | 3/2008 | Setzer et al. |
| 2008/0078390 A1 | 4/2008 | Milne et al. |
| 2008/0083644 A1 | 4/2008 | Janbakhsh et al. |
| 2008/0092894 A1 | 4/2008 | Nicolazzi et al. |
| 2008/0097234 A1 | 4/2008 | Nicolazzi et al. |
| 2009/0165795 A1 | 7/2009 | Nadjafizadeh et al. |
| 2009/0171176 A1 | 7/2009 | Andersohn |
| 2009/0205661 A1 | 8/2009 | Stephenson et al. |
| 2009/0205663 A1 | 8/2009 | Vandine et al. |
| 2009/0241952 A1 | 10/2009 | Nicolazzi et al. |
| 2009/0241953 A1 | 10/2009 | Vandine et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0247891 A1 | 10/2009 | Wood |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2010/0011307 A1 | 1/2010 | Desfossez et al. |
| 2010/0024820 A1 | 2/2010 | Bourdon |
| 2010/0051026 A1 | 3/2010 | Graboi |
| 2010/0051029 A1 | 3/2010 | Jafari et al. |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0139660 A1 | 6/2010 | Adahan |
| 2010/0147303 A1 | 6/2010 | Jafari et al. |

| | | |
|---|---|---|
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0236555 A1 | 9/2010 | Jafari et al. |
| 2010/0242961 A1 | 9/2010 | Mougel et al. |
| 2010/0288283 A1 | 11/2010 | Campbell et al. |
| 2010/0300446 A1 | 12/2010 | Nicolazzi et al. |
| 2011/0011400 A1 | 1/2011 | Gentner et al. |
| 2011/0023879 A1 | 2/2011 | Vandine et al. |
| 2011/0041849 A1 | 2/2011 | Chen et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138323 A1 | 6/2011 | Skidmore et al. |
| 2011/0146681 A1 | 6/2011 | Jafari et al. |
| 2011/0259330 A1 | 10/2011 | Jafari et al. |

OTHER PUBLICATIONS

7200 Ventilatory System: Addendum/Errata. Nellcor Puritan Bennett, Part No. 4-023576-00, Rev. A, Apr. 1988.

800 Operator's and Technical Reference Manual. Series Ventilator System, Nellcor Puritan Bennett, Part No. 4-070088-00, Rev. L, Aug. 2010.

840 Operator's and Technical Reference Manual. Ventilator System, Nellcor Puritan Bennett, Part No. 4-075609-00, Rev. G, Oct. 2006.

NUISANCE ALARM REDUCTION METHOD FOR THERAPEUTIC PARAMETERS

INTRODUCTION

A ventilator is a device that mechanically helps patients breathe by replacing some or all of the muscular effort required to inflate and deflate the lungs. During ventilation, the ventilator monitors various physiological parameters indicative of the patient's condition. Additionally, the ventilator monitors non-physiological parameters indicative of the mechanical operation of the therapeutic equipment in response to the patient's condition. The ventilator may be programmed to alarm when either monitored physiological or non-physiological parameters fall outside acceptable ranges.

Generally, alarms function to alert a clinician of an abnormal or unsafe condition that may impact the patient. In this sense, alarms are a very important and necessary feature of any therapeutic instrument. However, alarms may be considered a nuisance when they are not truly indicative of a need to intervene in the patient's treatment or to otherwise adjust the equipment. At best, nuisance alarms may cause clinicians unnecessary distraction from other patients and duties. At worst, nuisance alarms may cause clinicians to ignore legitimate alarm conditions to the detriment of a patient's well-being.

Nuisance Alarm Reduction Method for Therapeutic Parameters

This disclosure describes systems and methods for reducing nuisance alarms associated with monitoring non-physiological parameters in a ventilatory system.

Embodiments described herein seek to mitigate nuisance alarms by adjusting alarm conditions such that an alarm is not generated when a monitored parameter briefly falls outside an acceptable range by a slight degree, but such that an alarm is generated when a monitored parameter falls outside an acceptable range by a more significant magnitude and/or duration.

For example, embodiments may include methods and systems for reducing nuisance alarms while monitoring one or more non-physiological parameters in a ventilatory system. The method may comprise receiving alarm conditions, including a parameter threshold and an integral threshold, and monitoring at least one parameter of the one or more non-physiological parameters. Upon detecting a breach of the parameter threshold, calculating an integral of the breach and determining whether the integral of the breach is greater than the integral threshold.

The methods and systems may then generate an alarm when the integral of the breach is greater than the integral threshold.

In addition, embodiments may include a graphical user interface for configuring alarm conditions that reduce nuisance alarms on a ventilator. The graphical user interface may comprise at least one window and one or more elements within the at least one window. The one or more elements may comprise one or more input elements for enabling the clinician to input alarm settings for reducing nuisance alarms associated with monitoring one or more non-physiological parameters. The one or more elements may further comprise one or more selection elements for enabling the clinician to select graphic displays of alarm data collected while monitoring the one or more non-physiological parameters and/or preconfigured alarm settings for reducing nuisance alarms associated with monitoring the one or more non-physiological parameters.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The following drawing figures, which form a part of this application, are illustrative of described technology and are not meant to limit the scope of the invention as claimed in any manner, which scope shall be based on the claims appended hereto.

DETAILED DESCRIPTION

Although the techniques introduced above and discussed in detail below may be implemented for a variety of medical devices, the present disclosure will discuss the implementation of these techniques for use in a mechanical ventilator system. The reader will understand that the technology described in the context of a ventilator system could be adapted for use with other therapeutic equipment that generates nuisance alarms.

This disclosure describes systems and methods for reducing nuisance alarms associated with monitoring non-physiological parameters in a ventilatory system. Non-physiological parameters may include, but are not limited to, parameters that are internally monitored by the ventilator based on pre-configured ranges dictated by the manufacturer, by an applicable protocol, or by the clinician. The systems and methods presented herein are particularly useful for reducing nuisance alarms associated with clinically insignificant breaches of a parameter threshold, while generating relevant alarms associated with more substantial threshold breaches that indicate patient and/or equipment intervention may be appropriate.

Figure 1:
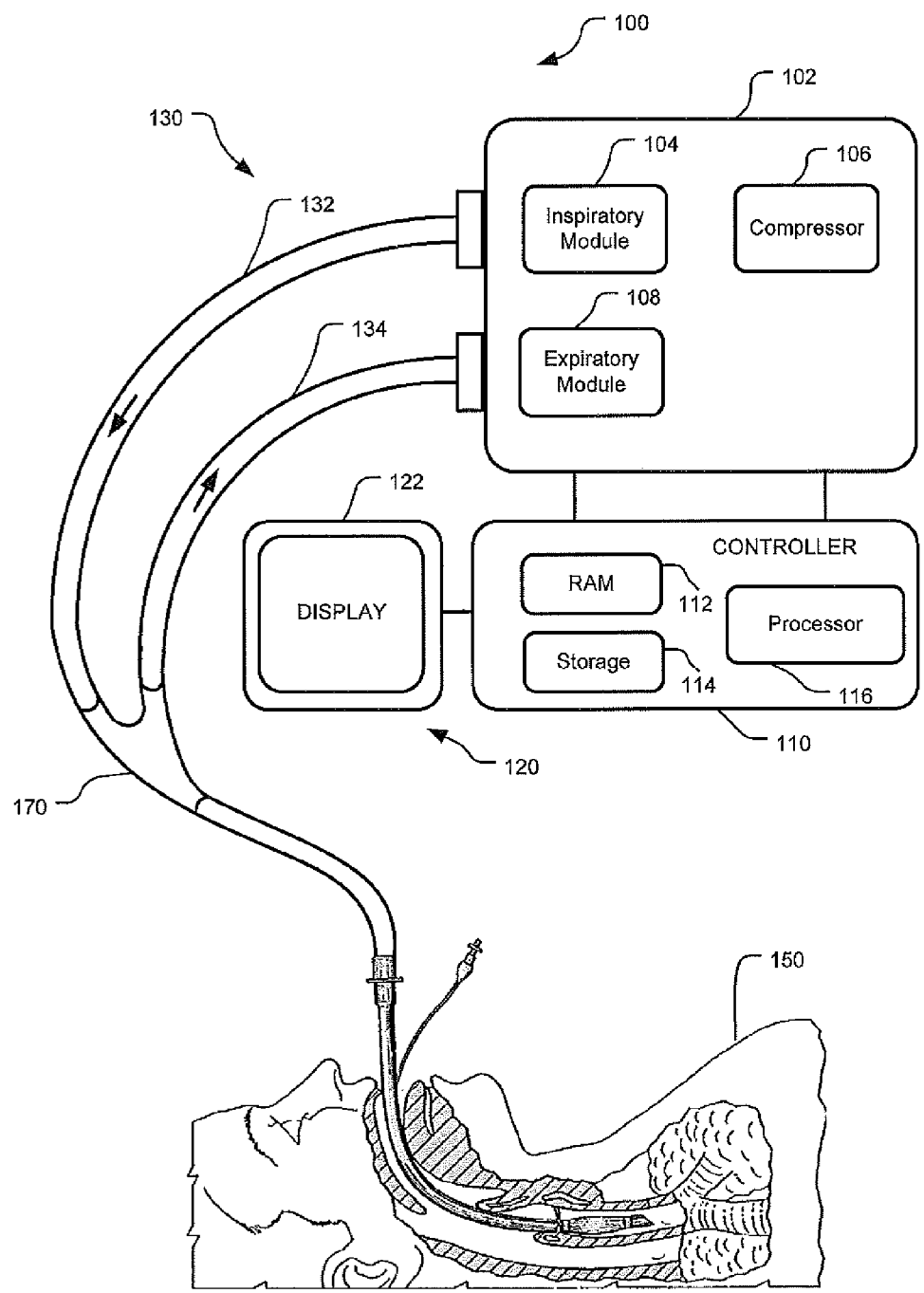
FIG. 1 is a diagram illustrating an embodiment of an exemplary ventilator connected to a human patient.

FIG. 1 illustrates an embodiment of a ventilator 100 connected to a human patient 150. Ventilator 100 includes a pneumatic system 102 (also referred to as a pressure generating system 102) for circulating breathing gases to and from patient 150 via the ventilation tubing system 130, which couples the patient to the pneumatic system via an invasive patient interface.

Ventilation tubing system 130 may be a two-limb (shown) or a one-limb circuit for carrying gas to and from the patient 150. In a two-limb embodiment, a fitting, typically referred to as a "wye-fitting" 170, may be provided to couple the patient interface to an inspiratory limb 132 and an expiratory limb 134 of the ventilation tubing system 130.

Pneumatic system 102 may be configured in a variety of ways. In the present example, system 102 includes an expiratory module 108 coupled with the expiratory limb 134 and an inspiratory module 104 coupled with the inspiratory limb 132. Compressor 106 or another source(s) of pressurized gases (e.g., air, oxygen, and/or helium) is coupled with inspiratory module 104 to provide a gas source for ventilatory support via inspiratory limb 132.

The pneumatic system may include a variety of other components, including sources for pressurized air and/or oxygen, mixing modules, valves, sensors, tubing, accumulators, filters, etc. Controller 110 is operatively coupled with pneumatic system 102, signal measurement and acquisition systems, and an operator interface 120 that may enable an operator to interact with the ventilator 100 (e.g., change ventilator settings, select operational modes, view monitored parameters, etc.). Controller 110 may include memory 112, one or more processors 116, storage 114, and/or other components of the type commonly found in command and control computing devices.

The memory 112 is non-transitory, computer-readable storage media that stores software that is executed by the processor 116 and which controls the operation of the ventilator 100. In an embodiment, the memory 112 includes one or more solid-state storage devices such as flash memory chips. In an alternative embodiment, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 116. Computer-readable storage media includes non-transitory, volatile and non-volatile, removable and non-removable media implemented in any method or technology for storage of information such as computer-readable instructions, data structures, program modules or other data. Computer-readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

As described in more detail below, controller 110 may monitor pneumatic system 102 in order to ensure proper functioning of the ventilator. The specific monitoring may be based on inputs received from pneumatic system 102 and sensors, operator interface 120, and/or other components of the ventilator. In the depicted example, operator interface includes a display 122 that may be touch-sensitive and/or voice-activated, enabling the display to serve both as an input and output device.

Figure 2:
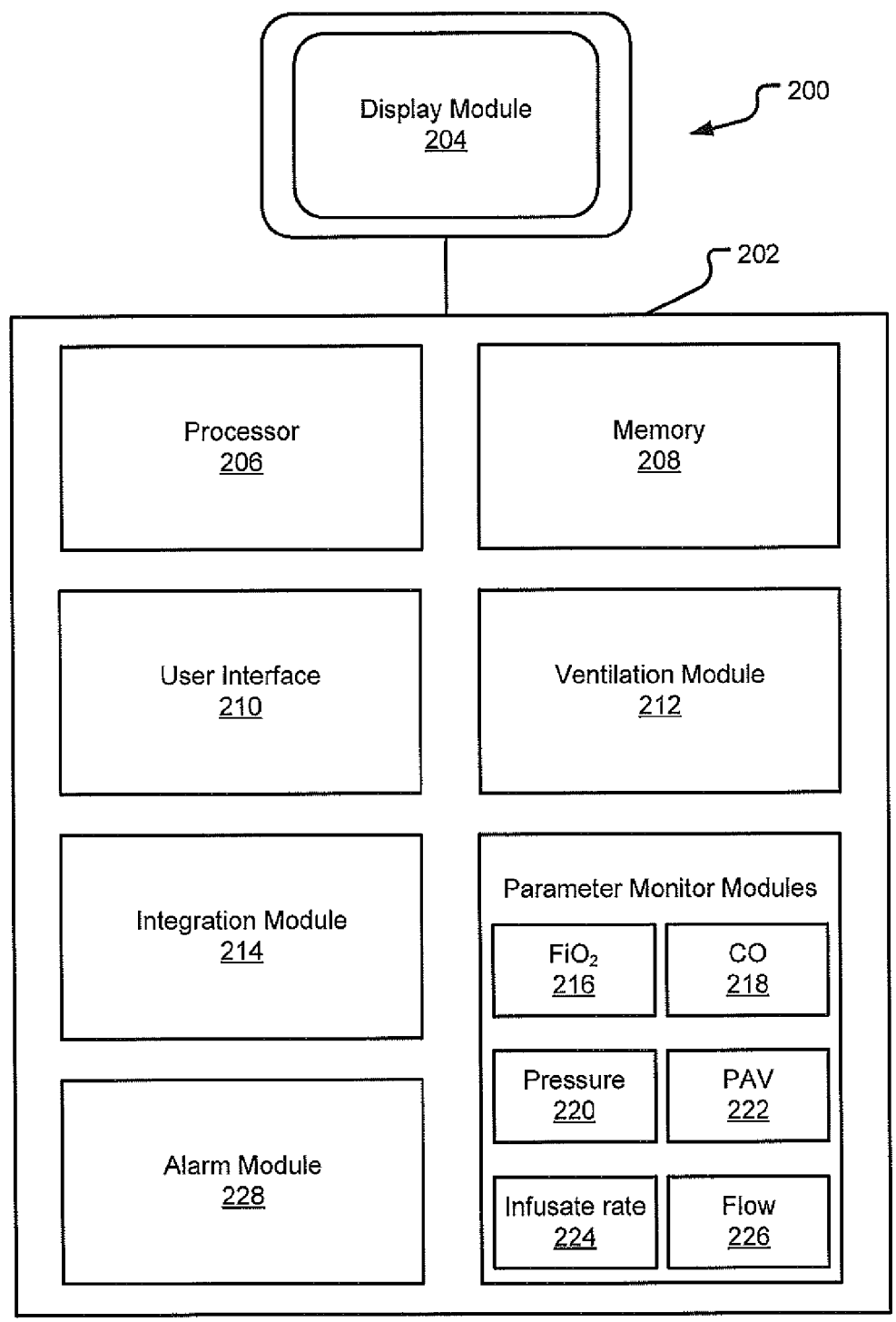
FIG. 2 is a block-diagram illustrating an embodiment of a ventilatory system for monitoring various non-physiological parameters and mitigating nuisance alarms associated therewith.

FIG. 2 is a block-diagram illustrating an embodiment of a ventilatory system 200 for monitoring various non-physiological parameters and mitigating nuisance alarms associated therewith.

The ventilator 202 includes a display module 204, memory 208, one or more processors 206, user interface 210, and ventilation module 212. Memory 208 is defined as described above for memory 112. Similarly, the one or more processors 206 are defined as described above for the one or more processors 116. Processors 206 may further be configured with a clock whereby elapsed time may be monitored by the system 200. Ventilation module 212 oversees ventilation as delivered to a patient according to the ventilatory settings prescribed for the patient.

The display module 204 displays various input screens to a clinician, including but not limited to one or more parameter input screens, as will be described further herein, for receiving clinician input. The display module 204 is configured to communicate with user interface 210. Specifically, display module 204 and user interface 210 may receive parameter threshold information from a clinician, as described further herein with reference to the "$FiO_2$ Input Screen" illustrated in FIG. 3. The user interface 210 may include a graphical user interface (GUI) and may provide various windows and elements to the clinician for input and interface command operations. Additionally, user interface 210 may provide useful information to the clinician through display module 204. This useful information may be in the form of various data regarding the operation of the ventilatory equipment, displaying for instance the automatically-adjusted $FiO_2$, carbon monoxide (CO) delivery, circuit pressure and flow, etc. Alternatively, useful information may be derived by the ventilator 202, based on data gathered from the various monitoring modules 216-226, and the useful information may be displayed in the form of graphs, wave representations, pie graphs, or other suitable forms of display to the clinician. Display module 204 may further be an interactive display, whereby the clinician may both receive and communicate information to the ventilator 202, as by a voice- or touch-activated display screen. Alternatively, user interface 210 may provide other suitable means of communication with the ventilator 202, for instance by a keyboard or other suitable interactive device.

Voice activation, e.g., via voice or speech recognition, may provide a means for converting sounds, words, and/or phrases of a clinician's voice into input recognized by the ventilator. More specifically, sounds or words may be detected by the ventilator and may be converted into electrical signals which may then be transformed into coding patterns understood by the computing components of the ventilator, including for instance the controller 110 and the one or more processors 116. Thus, the voice-activation feature may involve additional components and modules for providing input to the ventilator. For instance, additional components may include a microphone, for receiving sounds and/or words from the clinician, and an "analog-to-digital (A/D) converter," for converting the sounds and/or words into a digitized electrical signal. The voice-activation feature may also involve storing a digitized voice template in memory 112. The digitized voice template may be associated with coding patterns understood by the computing components, such as by voice-recognition software.

The voice-activation feature may further be "trained" by a particular clinician, that is, the ventilator may associate a particular clinician's voice with words and/or sounds stored in the digitized voice template by conducting a series of tests with that clinician. For example, the series of tests may include presenting one or more words of the digitized voice template to the clinician and requesting that the clinician say the one or more words into the microphone several times. Components of the ventilator may recognize patterns associated with the particular clinician's spoken word and may then associate these patterns with the sounds or words stored in the digitized voice template. Other embodiments may require no such "training" of a particular clinician and the digitized voice template may be associated with a suitable array of human voice patterns.

According to either embodiment, the digitized electrical signal received from the microphone when the clinician speaks a command may be compared with the digitized voice template stored in the ventilator memory. As mentioned previously, the digitized voice template is associated with coding patterns understood by the computing components. Various coding patterns may be recognized as any number of suitable inputs or commands for instructing the ventilator. Upon recognition of a particular input or command received via voice-activation from the clinician, the ventilator may respond accordingly, as described below regarding other modes of clinician input or communication.

As indicated above, user interface 210 may be configured to accept various parameter settings from the clinician. Alternatively, parameter settings may be dictated by default settings pre-configured according to a standard protocol, for instance a hospital-specific or physician-specific protocol. As will be described further herein with reference to FIG. 3, the clinician may enter parameter settings by accessing a parameter input screen from a main input display. Parameter input screens may be specific for each of many monitored non-physiological parameters. Alternatively, a single parameter input screen may be presented that incorporates one or more windows for selecting particular non-physiological parameters and one or more windows for accepting parameter settings and selections for the particular non-physiological parameters. Inputs for non-physiological parameters may include, but are not limited to, inputs regarding parameter high and low thresholds, integral threshold selections, integral fadeout selections, etc. Inputs may further include selections of various standardized settings or types of graphical display. Clinician input may be received at any suitable time during or before the ventilation of a patient.

Integration module 214 may determine an integral, or some function of an integral, based on parameter data received from monitor modules 216-226 and parameter threshold settings received from user interface 210 or based on standard default parameter threshold settings. In simple terms, an integral provides a means for combining a quantitative element with a durational element in order to determine more clinically-relevant alarm conditions for a particular parameter. As such, the integrated alarm conditions are designed to generate alarms only when a parameter falls outside a threshold by a clinically significant degree for a clinically significant amount of time.

An algorithm according to one embodiment may represent the integral as the difference between the parameter value and the parameter threshold value during a period of time that the parameter threshold is breached. For example, a simple time-based integral of non-physiological parameter p may be expressed as follows:

$$\int p(t) = \int p(t-1) + |Tp - p(t)| \qquad \text{Integral equation (1)}$$

Where $\int p(t)$ is the integral of parameter p at time t, p(t) is the parameter value at time t, and Tp is the parameter threshold setting for parameter p. In accordance with the present disclosure, user interface 210 may be further configured to accept an integral threshold setting, T$\int$, such that an alarm will sound when $\int p(t) > T\int$.

Monitoring modules 216-226 operate to monitor various non-physiological parameters associated with the proper mechanical operation of the ventilator. The monitoring modules 216-226 may access threshold parameter settings and parameter integral thresholds from the user interface 210 or may receive parameter integral information from the integration module 214. Alternatively, monitoring modules 216-226 may receive all parameter threshold and parameter integral threshold information directly from the integration module 214. Further, monitoring modules 216-226 may communicate directly with alarm module 228, or may communicate via integration module 214 with alarm module 228.

Monitoring modules 216-226 may utilize one or more sensors to detect changes in various non-physiological parameters. Specifically, the one or more sensors may be placed in any suitable internal location, within the ventilator itself, or in any suitable external location, within the ventilatory circuitry or other devices communicatively coupled to the ventilator. For example, sensors may be coupled to the inspiratory and/or expiratory modules for detecting changes in, for example, circuit pressure and flow. Additionally, the one or more sensors may be affixed to the ventilatory tubing or may be imbedded in the tubing itself. For example, pressure transducers may be attached at various locations along the ventilatory circuit to detect changes in circuit pressure and/or flow. Specifically, sensors may utilize optical or ultrasound techniques for measuring changes in circuit pressure and/or airflow. A patient's blood or expired gases may also be monitored by sensors to detect physiological changes that may impact the non-physiological parameters of interest, or that may indicate faults in the automatic ventilatory adjustment of non-physiological parameter settings. Sensors and other monitoring devices employed within the ventilatory equipment may be further utilized to detect faults in the mechanical operation of the ventilator, etc. Indeed, any sensory or derivative technique for monitoring the proper operation of the ventilator and for monitoring one or more non-physiological parameters of interest may be employed in accordance with embodiments described herein.

Specifically, fractional inspired oxygen (FiO$_2$) monitor module 216 may monitor and control FiO$_2$ based on an automatically-adjusted FiO$_2$ parameter setting. The FiO$_2$ parameter setting may be configured according to safety guidelines as determined by the manufacturer, by an applicable protocol, or by the clinician. FiO$_2$ monitor module 216 may determine FiO$_2$ based on readings from various sensors or other techniques, such as by pulse oximetery (SpO$_2$), as described above. When the FiO$_2$ parameter breaches a predetermined FiO$_2$ threshold setting, it may indicate that the gas diffusion within a patient's lungs has significantly changed. Ordinarily, an alarm is warranted to adjust the FiO$_2$ parameter setting and to prevent such long-term risks as hyperoxia. However, if the threshold breach is merely the result of a minor and brief change in FiO$_2$, for example due to the patient changing positions, an alarm may not be indicative of a clinically significant event and should not be generated. For example, a breach of a 60% FiO$_2$ threshold by 2% for two minutes would be an example of a likely insignificant threshold breach event. Alternatively, if the threshold breach is the result of significant changes in the physical condition of the patient over a period of time, or due to inappropriate or erroneous FiO$_2$ delivery by the ventilator over a period of time, an alarm is warranted. For example, a breach of a 60% $FiO_2$ threshold by 10% for ten minutes would be an example of a likely significant threshold breach event.

Carbon monoxide (CO) monitor module 218 may regulate delivery of trace amounts of CO to a patient during ventilation. CO may be delivered to the patient due to its versatile role as a signaling molecule. For example, CO may be administered by the ventilator according to preconfigured settings in concentrations of about 10-500 parts per million (ppm). CO monitor module 218 may be further preconfigured to automatically adjust CO delivery in response to changes in a patient's blood carboxyhemoglobin fraction. Measurements of the blood carboxyhemoglobin fraction may be obtained by any suitable means. Ordinarily, an alarm may be warranted to adjust the automated delivery of CO for breaching a low CO threshold (i.e., indicating a sub-therapeutic condition) or for breaching a high CO threshold (i.e., indicating a toxic condition). However, in either case, a minor and brief excursion by the ventilator above or below the CO threshold delivery settings would likely not be clinically significant, and as such, an associated nuisance alarm should be avoided.

Pressure monitor module 220 may monitor pressure within a ventilatory circuit. As the ventilator is responsible for delivering respiratory gases to the patient according to patient needs, the ventilator is configured to automatically adjust the delivery of gases in order to maintain circuit pressure within preset pressure ranges suitable for the patient. Specifically, the pressure monitor module 220 may take real-time measurements of circuit pressure and adjust gas delivery accordingly. Pressure monitor module 220 may monitor circuit pressure using sensors or other devices, as described above. Alternatively, pressure monitor module 220 may derive circuit pressure based on other data and measurements by using mathematical equations or otherwise. As circuit pressure monitoring may be useful to prevent barotrauma to the patient, ventilators may be preconfigured with various high-pressure alarm criteria. For example, ventilators may be configured to alarm based on an excursion above a preset pressure threshold for a certain number of breaths or for a certain amount of time. Further, ventilators may be configured to escalate alarm priority based on the length of time and/or the magnitude a pressure threshold has been exceeded. Improvements disclosed herein seek to eliminate the need for monitoring multiple alarm criteria, i.e., a pressure threshold and a number of breaths threshold, by combining the criteria into a single time-integral or breath-integral threshold. For example, a single breath-integral may be expressed as pressure-breaths or a single time-integral may be expressed as pressure-minutes, such that the integral is indicative of both the extent and the duration of an excursion outside the pressure integral threshold amount. Present embodiments may further disclose implementing alarm priorities by configuring low (e.g., 10 $H_2O$ cm-breaths), medium (e.g., 20 $H_2O$ cm-breaths), and high (e.g., 40 $H_2O$ cm-breaths) pressure integral threshold settings.

Pressure monitor module 220 may also be relevant to detecting occlusion in a ventilatory circuit. As such, a plurality of pressure measurements may be made over a predetermined time period and may then be compared to predetermined pressure thresholds in order to detect occlusion within the circuit. According to present embodiments, a pressure integral threshold may be employed in order to simplify the detection of occlusion. For example, a time-integral between a measured pressure and pressure threshold may be combined in a pressure integral threshold setting. Specifically, a pressure integral threshold may be set to 1000 cm $H_2O$-ms, i.e., an alarm will be generated when pressure exceeds a pressure threshold by 20 cm $H_2O$ for 50 ms, exceeds a pressure threshold by 10 cm $H_2O$ for 100 ms, or exceeds a pressure threshold by 50 cm $H_2O$ for 20 ms, etc.

The Proportional Assist Ventilation (PAV) monitor module 222 may automatically adjust a Percent Support or a Pressure Support setting based on various respiratory parameters. For example, the PAV monitor module may adjust Percent Support or Pressure Support based on a Work-of-Breathing (WOB) estimate. In this example, the ventilator may make automatic adjustments in support in order to maintain the patient's WOB at a level that is adequate for exercising the patient's lungs without causing exhaustion. The WOB estimate itself may be determined based on real-time estimates of the patient's lung compliance and airway resistance, for example. However, errors in these real-time estimates may correspondingly lead to errors in the WOB estimate, resulting in an improper adjustment of Percent Support or Pressure Support. When an automatically-adjusted Percent Support setting falls above predetermined limits, it may indicate that the patient's condition has declined or, alternatively, an error in adjustment may cause the patient to over-inflate his or her lungs. When an automatically-adjusted Percent Support setting falls below predetermined limits, an error in adjustment may result in insufficient respiratory support that may overwork the patient's diaphragm. As such, high and low threshold limits are relevant to the proper adjustment of ventilatory support. However, in an effort to mitigate nuisance alarms, only significant adjustments in support should alert the clinician, for example, based on significant fluctuations in a WOB estimate. Alternatively, minor and/or brief fluctuations in the WOB estimate may not be clinically significant and correspondingly minor adjustments in Percent Support or Pressure Support should not generate alarms.

Embodiments disclosed herein may incorporate an integral alarm threshold for PAV that combines PAV Percent Support or Pressure Support thresholds with a time element. For example, a high integral threshold for PAV Percent Support may be represented as 300 percent-minutes, i.e., an alarm will be generated for Percent Support of 20% above high threshold for 15 minutes, or for Percent Support of 10% above high threshold for 30 minutes, or for Percent Support of 5% above high threshold for 60 minutes. A low integral threshold for PAV Percent Support may be represented as 100 percent-minutes, i.e., an alarm will be generated for Percent Support of 20% below low threshold for 5 minutes, or for Percent Support of 10% below low threshold for 10 minutes, or for Percent Support of 5% below low threshold for 20 minutes. Additionally, high and low integral alarm thresholds for PAV Pressure Support may be represented as 100 cm $H_2O$-minutes, i.e., an alarm will be generated for a Pressure Support of 20 cm $H_2O$ above or below threshold limits for 5 minutes, or for a Pressure Support of 10 cm $H_2O$ above or below threshold limits for 10 minutes, or for Pressure Support of 5 cm $H_2O$ above or below threshold limits for 20 minutes.

Infusate rate monitor module 224 may regulate the rate of delivery of various infusates to a patient during ventilation. Specifically, the ventilator may be configured to automatically adjust infusion rate based on changes in a physiological parameter indicative of the therapeutic affects of the infusate. Ventilators may be further configured with high- and low-threshold alarm settings corresponding to the automatically adjusted infusion rates. However, there is a potential for nuisance alarms resulting from brief, minor excursions above or below threshold alarm settings due to normal physiological variability. As such, embodiments disclosed herein may incorporate an integral alarm threshold for infusate rates that combines the high- and low-threshold settings with a time element. Thus, nuisance alarms resulting from brief, minor excursions above or below predetermined infusate rate thresholds may be avoided, while clinically relevant deviations from threshold settings, resulting from infusate rate adjustments of substantial magnitude and duration, will generate an alert.

For example, an exemplary ventilator may comprise an insulin pump for delivering insulin to a patient in response to a blood glucose level. The rate of insulin delivery may be automatically adjusted by the ventilator based on fluctuations in the blood glucose level. The ventilator may be further configured with high- and low-threshold settings for insulin delivery according to safety guidelines as determined by the manufacturer, by an applicable protocol, or by the clinician. Present embodiments may combine the predetermined high- and low-threshold settings for insulin delivery with a time element, resulting in an insulin integral threshold. The ventilator is further configured with the insulin integral threshold such that only deviations in insulin delivery of significant magnitude and/or duration generate alarms.

By way of another example, an exemplary ventilator may comprise an IV pump for delivering analgesics or anesthetics to a patient in response to physiological indications, such as an electroencephalogram (EEG) measurement indicating consciousness, or measurements indicating respiratory depression or apnea. The rate of analgesic or anesthetic delivery may be automatically adjusted by the ventilator based on fluctuations in these physiological indicators. The ventilator may be further configured with high- and low-threshold settings for automatic analgesic or anesthetic delivery based on safety guidelines as determined by the manufacturer, by an applicable protocol, or by the clinician. Present embodiments may combine the predetermined high- and low-threshold settings for analgesic or anesthetic delivery with a time element, resulting in an analgesic or anesthetic integral threshold. The ventilator is further configured with the analgesic or anesthetic integral threshold such that only deviations in automatic delivery of significant magnitude and/or duration generate alarms.

Flow monitor module 226 may monitor airflow within a ventilatory circuit. Airflow into and out of the lungs is governed by a pressure gradient between the lungs and the external atmospheric pressure. The greater the pressure gradient, the greater the resultant flow into or out of a patient's lungs. Flow may be directly measured or may be derived from pressure readings according to any suitable method either currently known or disclosed in the future. The ventilator may be further configured with flow threshold settings for detecting leaks in the ventilatory circuit. Random fluctuations in flow measurements or actual airflow that create small, brief excursions beyond flow thresholds may occur, but these brief fluctuations likely do not require caregiver intervention and would likely generate nuisance alarms. Alternatively, sufficiently large and sustained variations in flow may indicate leaks and should alert the clinician that patient and/or equipment intervention may be necessary. Embodiments of the present application may simplify the detection of leaks by calculating a time integral wherein measured flow readings fall outside threshold levels. For example, a flow integral threshold may be set to 25 percent-minutes, i.e., an alarm will be generated indicating a leak when flow measurements are 25% of delivered flow for 1 minute, 50% of delivered flow for 30 seconds, or 10% delivered flow for 2½ minutes.

Alarm module 228 may determine when an appropriate alarm should be generated for alerting a clinician that patient and/or equipment intervention may be indicated. Alarm module 228 may be in communication with integration module 214 and/or parameter monitor modules 216-226 in order to avoid generating nuisance alarms that may detract from optimal patient care. For example, alarm module 228 may receive an indication from the integration module 214 and/or parameter monitor modules 216-226 that a parameter integral threshold has been breached. The breach of a parameter integral threshold, in turn, may indicate that a parameter threshold has been breached by a clinically significant magnitude for a clinically significant amount of time.

Alarm module 228 may be configured to generate any type of suitable signal for alerting the clinician that patient and/or equipment intervention may be warranted. The type of signal may be visual, such as a blinking light represented on a graphical display in a nursing station, on a visual display on the ventilator, or by any other visual indicator communicating an alert to one or more clinicians in connection with the ventilated patient. Alternatively, the signal may be audio, such as a bell, beep, buzz, siren, or other suitable auditory signal for alerting the clinician that patient and/or equipment intervention may be indicated. Further still, the alert may be any appropriate combination of visual and audio signals, or any other appropriate means or method for alerting the clinician. Alarm module 228 may also be in communication with user interface 210 such that clinician input regarding a preferred type of alert may be communicated to alarm module 228.

Figure 3:
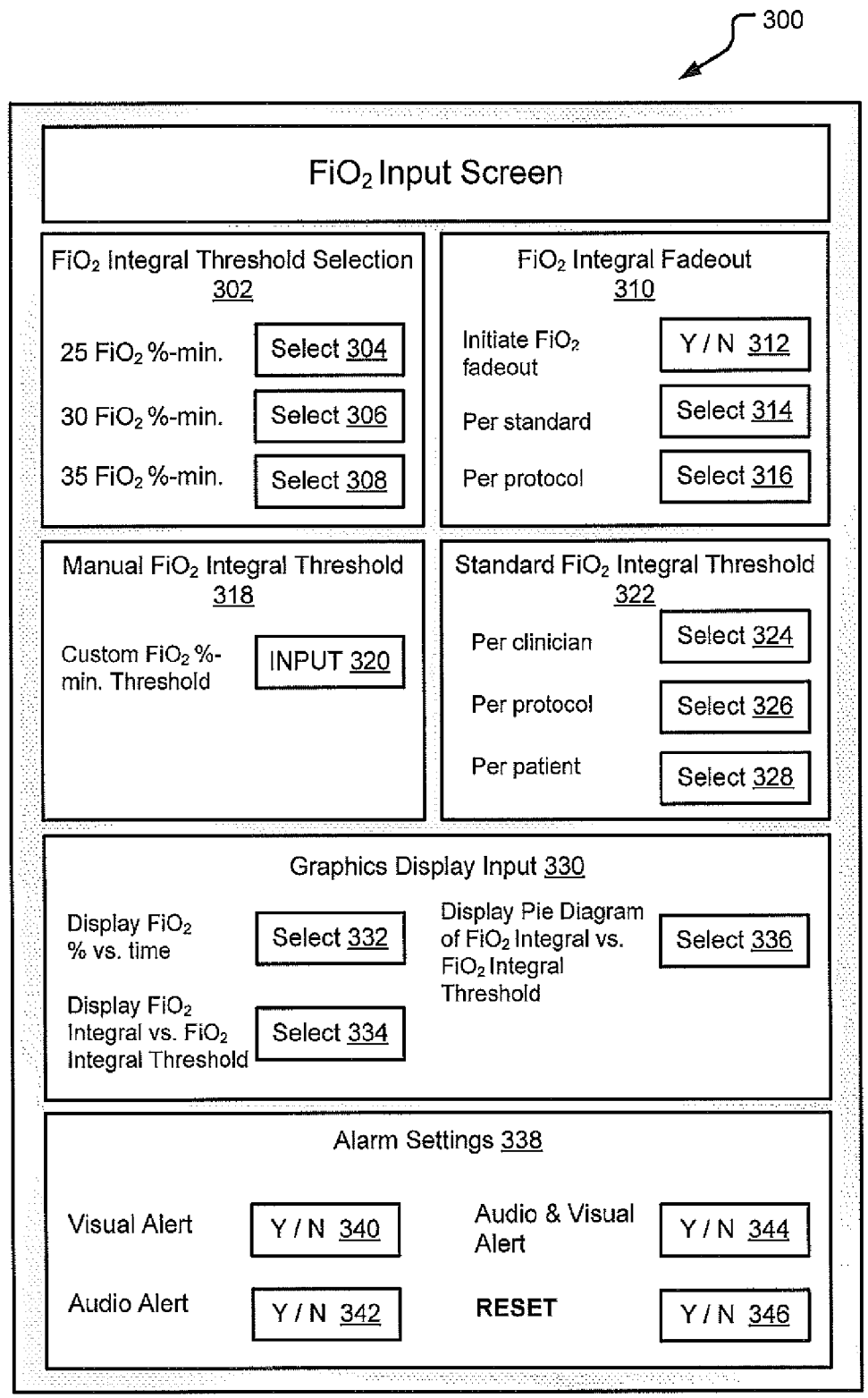
FIG. 3 is an illustration of an embodiment of a graphical user interface for receiving clinician input for monitoring $FiO_2$ such that nuisance alarms are reduced.

FIG. 3 is an illustration of an embodiment of a graphical user interface for receiving clinician input for monitoring a non-physiological parameter such that nuisance alarms are reduced. Specifically, FIG. 3 illustrates an embodiment of a "$FiO_2$ Input Screen," as described above with reference to display module 204.

The disclosed embodiment of the $FiO_2$ Input Screen 300 displays various input categories, or windows, and entry or command portals, or elements, wherein a clinician may communicate parameters and commands to the ventilator. Disclosed windows and elements may be arranged in any suitable order or configuration such that information may be communicated by the clinician to the ventilator in an efficient and orderly manner. Windows disclosed in the illustrated embodiment of the $FiO_2$ Input Screen 300 may be configured with elements for accessing alternative display input screens or graphical display screens as may be provided by the ventilator. Disclosed windows and elements are not to be understood as an exclusive array, as any number of similar suitable windows and elements may be displayed for the clinician within the spirit of the present disclosure. Further, the disclosed windows and elements are not to be understood as a necessary array, as any number of the disclosed windows and elements may be appropriately replaced by other suitable windows and elements without departing from the spirit of the present disclosure. The illustrated embodiment of the $FiO_2$ Input Screen 300 is provided as an example, including potentially useful windows and elements that may be provided to the clinician to facilitate the input of selections and commands relevant to reducing nuisance alarms while monitoring non-physiological parameters, as described herein.

Further embodiments of the $FiO_2$ Input Screen 300 may include, for example, an optional alarm event log that may display a history of alarm events for subsequent clinical review. This optional alarm event log (not shown) may provide the clinician with useful information for altering integral alarm thresholds, etc.

In $FiO_2$ integral threshold selection window 302, a selection element 304 may be provided wherein a clinician may choose 25 $FiO_2$%-min. as the integral threshold setting for $FiO_2$ delivery, as discussed above. In this case, an alarm generates when $FiO_2$ delivery exceeds 25% $FiO_2$ for 1 minute, etc., as described above. Alternatively, the clinician may initiate selection element 306, wherein 30 $FiO_2$%-min. is chosen as the integral threshold setting for $FiO_2$ delivery, as discussed above. Finally, in accordance with the disclosed embodiment, the clinician may initiate selection element 308, wherein 35 $FiO_2$%-min. is chosen as the integral threshold setting for $FiO_2$ delivery, as discussed above. In the spirit of the present disclosure, the ventilator may be preconfigured to present any number of selection elements, providing any number of suitable integral threshold settings to the clinician for selection, as determined by the manufacturer, an applicable protocol, or otherwise.

In $FiO_2$ integral fadeout window 310, an element may be provided wherein a clinician may initiate an integral fadeout feature. Fadeout provides a method for increasing the sensitivity of the integral threshold to periodic threshold breach events. As described above, employing integrals and integral thresholds reduces nuisance alarms by focusing alarm conditions on threshold breaches that are significant in magnitude and/or duration. In general, the integral of each threshold breach is considered an isolated event. That is, if the integral of the threshold breach does not surpass the integral threshold setting, an alarm will not be generated. However, in certain situations, where a number of minor, short lived breaches occur in close succession, an alarm may be appropriate. The fadeout feature allows the integrals of closely occurring minor threshold breaches to be merged such that the integral threshold may be breached where appropriate.

For example, the integral equation above may be adjusted to increase sensitivity to closely occurring breach events as follows:

$$\int p(t) = \int p(t-1) + |W(Tp - p(t))| \qquad \text{Integral fadeout equation (2)}$$

Here again, $\int p(t)$ is the integral of parameter p at time t, $p(t)$ is the parameter value at time t, and Tp is the threshold value setting for parameter p. As discussed above, when the integral, $\int p(t)$, surpasses an integral threshold, $T\!\!\int$, an alarm is generated. In cases where an alarm is generated, the system operates according to integral equation 1. That is, the integral $\int p(t)$ is not faded out, but is reset to zero following alarm generation.

Alternatively, fadeout becomes relevant where a threshold breach has occurred, but the integral threshold, $T\!\!\int$, has not been exceeded. According to the integral fadeout equation, a weighted constant, W, may be incorporated to "fadeout," or incrementally reduce, the parameter integral. Specifically, the parameter integral, $\int p(t)$, is bounded by a lower value of zero and an upper value of the integral threshold, $T\!\!\int$, where an alarm is generated when $\int p(t) > T\!\!\int$, as discussed above. In the case of fadeout, for a first threshold breach, $b_1$, where $\int p(t)_1$ is less than $T\!\!\int$, the fadeout constant, W, operates to reduce the $b_1$ integral by the weighted difference between Tp and p(t) until the integral reaches zero. However, if another threshold breach, $b_2$, occurs before $\int p(t)_1$ fades to zero, then $\int p(t)_1$ may be merged with $\int p(t)_2$. In that case, an alarm will be generated if $\int p(t)_1 + \int p(t)_2 > T\!\!\int$.

Referring again to the $FiO_2$ integral fadeout window 310, an element 312 may be provided wherein a clinician may initiate the integral fadeout feature. The fadeout feature may be configured with a predetermined constant, W, in accordance with manufacturer safety guidelines or other suitable determinations. Alternatively or additionally, selection element 314 may be provided such that the clinician may choose a particular standard, protocol, or otherwise, for determining a degree of sensitivity to successive threshold breach events.

Alternatively or additionally, input element 316 may enable the clinician to manually enter a particular weighted constant, W, either directly or according to a sensitivity scale, for designating a degree of sensitivity to successive threshold breach events. Additional selection and input elements for enabling the clinician to define and regulate the fadeout feature are well within the spirit of the present disclosure.

In manual $FiO_2$ integral threshold window 318, an input element 320 may be provided wherein a clinician may enter a custom $FiO_2$ integral threshold. As such, the clinician may enter any suitable $FiO_2$ integral threshold in the form of %-min., or other appropriate designation. In this case, an alarm will be generated when the $FiO_2$ integral breaches the manual $FiO_2$ integral threshold, as described above.

Alternatively or additionally, a standard $FiO_2$ integral threshold window 322 may be provided such that the clinician may select an appropriate $FiO_2$ integral threshold according to, for example, clinician orders at selection element 324, a particular protocol at selection element 326, or a prescription for a particular patient at selection element 328. Any additional selection elements for enabling the clinician to designate or select predetermined $FiO_2$ integral thresholds suitable for a patient are also well within the spirit of the present disclosure.

Figure 4A:
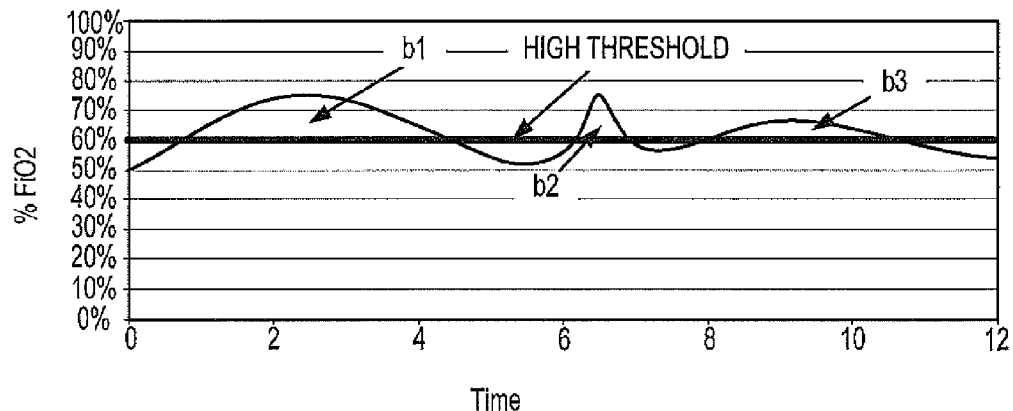
FIG. 4A is a line graph illustrating an embodiment corresponding to a plurality of breaches of a $FiO_2$ high threshold in a ventilatory system.
Figure 4B:
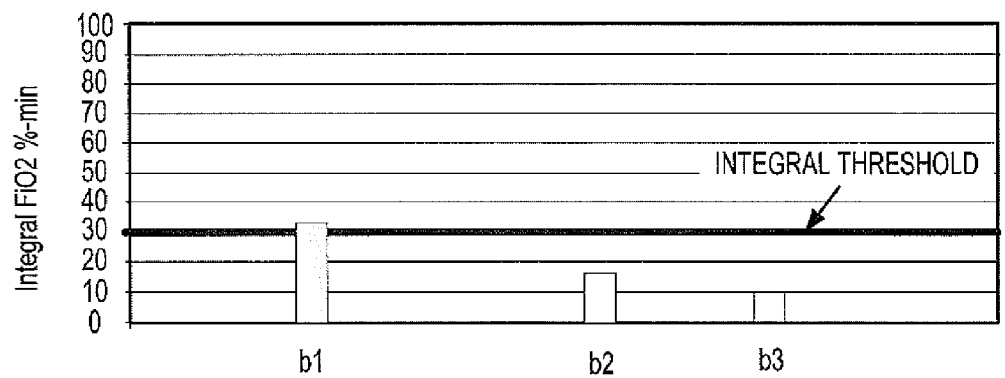
FIG. 4B is a bar graph illustrating an embodiment corresponding to a plurality of integral approximations of the plurality of breaches of the $FiO_2$ high threshold of FIG. 4A.

Graphics display input window 330 may provide elements wherein a clinician may select any number of graphical representations of $FiO_2$, $FiO_2$ threshold, and $FiO_2$ integral threshold data. Specifically, the clinician may select a graphical display of the $FiO_2$% data versus time at selection element 332. The clinician may alternatively or additionally select a graphical display of the $FiO_2$ integral data versus the $FiO_2$ integral threshold at selection element 334. FIGS. 4A and 4B provide an exemplary illustration of both a graphical display of $FiO_2$% data versus time and of the $FiO_2$ integral data versus the $FiO_2$ integral threshold. The clinician may alternatively or additionally select a pie diagram display of the $FiO_2$ integral versus the $FiO_2$ integral threshold at selection element 336. The $FiO_2$ Input Screen 300 may be further configured to offer other suitable and useful graphical display representations of the $FiO_2$% data, the $FiO_2$ integral data, and the $FiO_2$ integral threshold setting, as well as any other suitable comparison display that may be useful to the clinician.

An alarm settings window 338 may also be provided wherein a clinician may designate a type of alarm desired and may manually reset an alarm. For example, the clinician may designate a visual alert at selection element 340, an audio alert at selection element 342, or an audio/visual alert at selection element 344. Provision of alternative or additional elements for selecting any suitable type of alert is well within the present disclosure. Alarm settings window 338 may also provide an alarm reset element 346 wherein the clinician may reset any active alarm upon appropriate patient and/or equipment intervention or observation.

The above described windows and elements are provided merely as examples of potentially suitable user-interface options for reducing nuisance alarms while monitoring various non-physiological parameters, for example, the automatic adjustment of $FiO_2$.

As described previously, an individual user-interface input screen may be provided for each parameter of interest or a single universal parameter input screen may be provided that includes selections for any number of monitored non-physiological parameters. For example, similar to the exemplary $FiO_2$ Input Screen, individual user-input screens may be provided for minimizing nuisance alarms in CO delivery, circuit pressure regulation, PAV support adjustment, occlusion and/or leak detection, infusate delivery, etc. Alternatively, selections for each of these parameters may be provided in a universal parameter input screen.

As disclosed above for the $FiO_2$ Input Screen, a plurality of parameter input screens may display various input categories, or windows, and entry or selection portals, or elements, wherein a clinician may communicate input, selections, and commands to the ventilator for minimizing nuisance alarms associated with monitoring and regulating other non-physiological parameters. Among other things, appropriate parameter thresholds and parameter integral thresholds may be configured for the various non-physiological parameters of interest, as described above with reference to monitor modules 216-226 and integration module 214. Alternatively or additionally, selections for parameter integral fadeout may be provided, as described above with reference to $FiO_2$ integral fadeout window 310; selections to employ manual or standard parameter integral threshold settings may be provided, as described above with reference to windows 318 and 322; selections of various graphical representations for parameter and parameter threshold data may be provided, as described above with reference to window 330; and selections for alarm types may be provided, as described above with reference to window 338. Additional windows and elements, representing additional categories of input and additional input elements, maybe added as suitable or necessary for each parameter of interest without straying from the spirit of the disclosure.

FIG. 4A is a line graph illustrating an embodiment corresponding to a plurality of breaches of a $FiO_2$ high threshold that, ordinarily, would each result in an alarm. These breaches may be represented as $b_1$, $b_2$, and $b_3$, respectively.

As illustrated in FIG. 4A, for the first breach, $b_1$, $FiO_2$ percent exceeds a high threshold value by what may be considered a substantial amount for a significant period of time. For the second breach, $b_2$, the $FiO_2$ percent exceeds the high threshold by nearly the same magnitude as $b_1$, but for a shorter period of time. Finally, for the third breach, $b_3$, the $FiO_2$ percent exceeds the high threshold by a small magnitude, but for a longer period of time.

As discussed above, under traditional $FiO_2$ monitoring settings, each of the above-mentioned breaches would generate an alarm. However, two of these breaches, i.e., $b_2$ and $b_3$, may not be considered clinically significant because they occurred either for a short amount of time or by a slight degree. As a result, the alarms generated by these breaches may be considered nuisance alarms.

FIG. 4B is a bar graph illustrating an embodiment corresponding to a plurality of integral approximations of the breaches of the $FiO_2$ high threshold, i.e., $b_1$, $b_2$, and $b_3$, from FIG. 4A. Specifically, FIG. 4B illustrates a reduction of nuisance alarms such that brief and/or minor breaches of the $FiO_2$ high threshold, as illustrated in FIG. 4A, do not breach an integral threshold setting and, thus, do not generate nuisance alarms.

The $FiO_2$ integral may be defined as the area under the $FiO_2$ percent curve where the $FiO_2$ percent is greater than the $FiO_2$ high threshold, as illustrated in FIG. 4A. As can be seen by the bar-representations of integrals for breaches $b_1$, $b_2$, and $b_3$, both the magnitude and the duration of each breach impact the integral. Thus, where the first breach exceeded the $FiO_2$ high threshold by a significant degree for a significant period of time, the bar-represented integral of the first breach also exceeds an integral threshold setting, as illustrated in FIG. 4B. As such, breach $b_1$ would generate an alarm. Alternatively, the second breach, which breached the $FiO_2$ high threshold by a significant degree, but only for a short period of time, the bar-represented integral of the second breach does not exceed the integral threshold setting. Thus, according to this embodiment, breach $b_2$ would not generate an alarm. Finally, the third breach, which breached the $FiO_2$ high threshold by a slight degree, but for a longer period of time, the bar-represented integral of the third breach also does not exceed the integral threshold setting and will also not generate an alarm.

It should be appreciated that similar illustrations of how the use of parameter integral threshold settings may reduce nuisance alarms associated with minor and/or brief breaches of parameter thresholds may be presented for any number of non-physiological parameters monitored by a ventilatory system. For instance, graphic representations similar to FIGS. 4A and 4B may be provided for data associated with CO delivery, circuit pressure regulation, PAV support adjustments, occlusion and/or leak detection, infusate delivery, etc.

Figure 5:
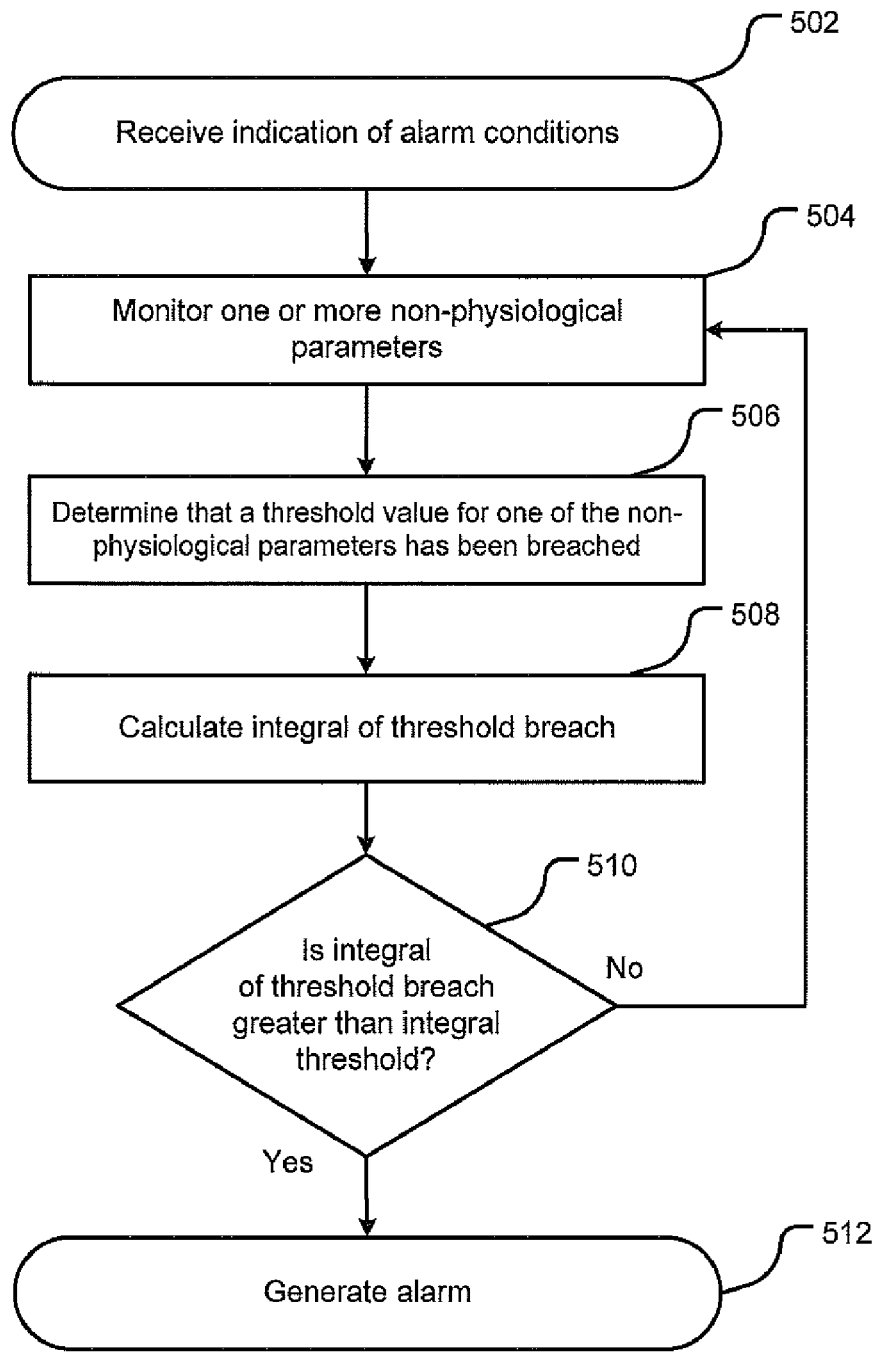
FIG. 5 is a flow chart illustrating an embodiment of a method for reducing nuisance alarms associated with regulating non-physiological parameters in a ventilatory system.

FIG. 5 is a flow chart illustrating an embodiment of a method for reducing nuisance alarms associated with regulating non-physiological parameters in a ventilatory system.

At receive indication of alarm conditions operation 502, the ventilator may receive settings, as described above, for reducing nuisance alarms associated with regulating non-physiological parameters during ventilation of a patient. Alarm condition settings may be preconfigured according to manufacturer guidelines or according to an applicable protocol, or alarm condition settings may be received as input from a clinician. Clinician input may be received at any suitable time prior to or during ventilation of a patient, i.e., it may be set during the initial ventilator set-up, or at any suitable time during a monitor operation 504. As has been described previously with reference to FIG. 3, the clinician may configure alarm condition settings by accessing a parameter input screen, for example, from a main ventilation input display. Appropriate alarm condition settings may include, among other things, an appropriate parameter threshold and an appropriate parameter integral threshold. Additionally, selections of suitable graphical displays and alarm types may be received.

At monitor non-physiological parameters operation 504, the ventilator may monitor one or more non-physiological parameters associated with the proper operation of a ventilator. As described above with reference to monitor modules 216-226, the ventilator may monitor and regulate the various non-physiological parameters according to any suitable method.

At determine threshold breach operation 506, the ventilator determines that a threshold setting of one of the monitored non-physiological parameters has been breached. As discussed previously with reference to monitor modules 216-226, the ventilator may determine that a parameter threshold has been breached by any suitable method.

At calculate integral of threshold breach operation 508, the ventilator may be configured to calculate an integral associated with the magnitude and the duration of the threshold breach determined at operation 506. For example, the integral may be calculated according to the first integral equation, as discussed with reference to integration module 214. Alternatively, the integral of a parameter threshold breach may be calculated according to any suitable equation as dictated by the manufacturer, an applicable protocol, or the clinician.

At decision operation 510, the ventilator evaluates whether the integral of the parameter threshold breach, as calculated in operation 508, has breached a parameter integral threshold setting. As discussed above, the parameter integral threshold setting may be received at operation 502 by any suitable means. Further, the ventilator may determine that the parameter integral has breached the parameter integral threshold according to any appropriate evaluation.

If the ventilator determines that the parameter integral threshold has been breached, the method continues to 512. Alternatively, if the ventilator determines that the integral threshold has not been breached, the method returns to monitor operation 504, as described above.

At generate alarm operation 512, the ventilator generates an alarm corresponding to the breach of a parameter integral threshold, as determined at decision operation 510. The type of alarm may be any suitable alarm for alerting the clinician that patient and/or equipment intervention may be necessary. The type of alarm may be configured by the manufacturer, or may be configured according to an applicable hospital policy, direct clinician input, or otherwise.

It should be appreciated that similar methods for utilizing parameter integral threshold settings to reduce nuisance alarms associated with minor and/or brief breaches of parameter thresholds may be provided for any number of non-physiological parameters monitored by a ventilatory system. For instance, the method described with reference to FIG. 5 may be appropriately applied to the ventilatory regulation of $FiO_2$ delivery, CO delivery, circuit pressure regulation, PAV support adjustments, occlusion and/or leak detection, infusate delivery, etc.

Figure 6:
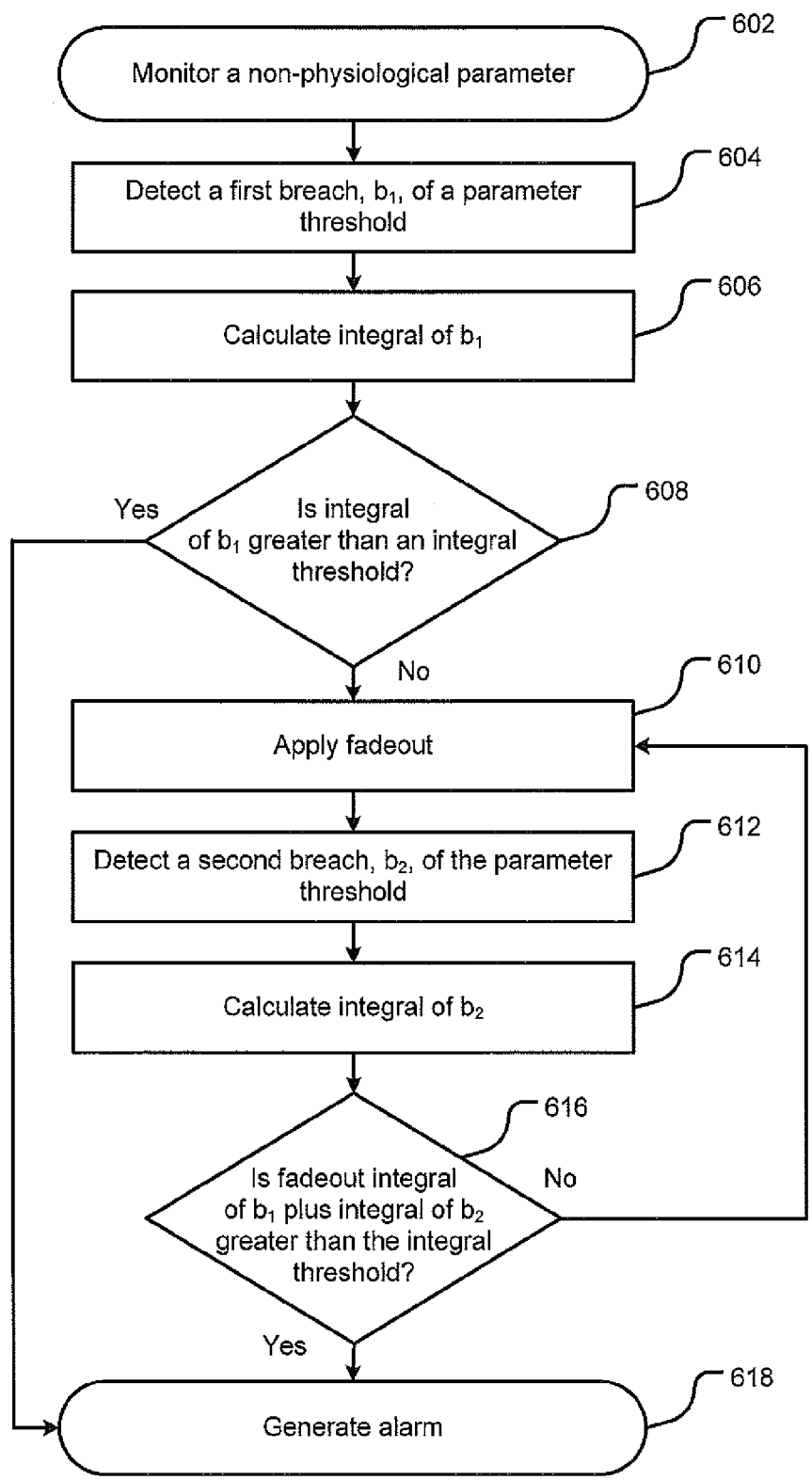
FIG. 6 is a flow chart illustrating an embodiment of a method for employing a fadeout operation for increasing sensitivity to periodic breach events while reducing nuisance alarms associated with regulating non-physiological parameters in a ventilatory system.

FIG. 6 is a flow chart illustrating an embodiment of a method for employing a fadeout operation for increasing sensitivity to multiple periodic breach events while reducing nuisance alarms associated with regulating non-physiological parameters in a ventilatory system.

At monitor non-physiological parameter operation 602, the ventilator may monitor a non-physiological parameter according to any suitable method, as described above with reference to monitor operation 504.

At detect first breach operation 604, the ventilator detects that the value of a monitored parameter has breached a parameter threshold. For simplicity, the first breach is designated $b_1$.

At calculate integral of $b_1$ operation 606, the ventilator calculates an integral associated with the magnitude and the duration of $b_1$.

At decision operation 608, the ventilator evaluates whether the integral of $b_1$, as calculated in operation 606, has breached an integral threshold setting. If $b_1$ has breached the integral threshold, the methods continue to generate alarm operation 618. Alternatively, if $b_1$ has not breached the integral threshold, the methods continue to operation 610.

At apply fadeout operation 610, the ventilator applies a weighted constant to the integral of $b_1$ such that the integral of $b_1$ may be incrementally reduced after $b_1$ ends. For example, the ventilator may decrease the integral of $b_1$ according to an integral fadeout equation as described above with reference to $FiO_2$ integral fadeout window 310. Alternatively, the integral fadeout of $b_1$ may be calculated according to any suitable equation as dictated by the manufacturer, an applicable protocol, or the clinician.

At detect second breach operation 612, the ventilator detects that the value of a monitored parameter has breached the parameter threshold a second time. For simplicity, the second breach is designated $b_2$.

At calculate integral of $b_2$ operation 614, the ventilator calculates an integral associated with the magnitude and the duration of $b_2$.

At decision operation 616, the ventilator evaluates whether the fadeout integral of $b_1$, as applied at operation 610, plus the integral of $b_2$, as calculated at operation 614, has breached the integral threshold setting. If the fadeout integral of $b_1$ plus the integral of $b_2$ breaches the integral threshold, the methods continue to generate alarm operation 618. Alternatively, if the fadeout integral of $b_1$ plus the integral of $b_2$ has not breached the integral threshold, the methods may return to apply fadeout operation 610. In this case, fadeout may be applied to both the fadeout integral of $b_1$ and the integral of $b_2$, as described above.

It should be appreciated that, as discussed above with reference to the integral fadeout equation, each successive breach integral may be incrementally decreased based on, for example, a weighted constant, W. As such, multiple breach integrals may be merged wherein additional threshold breaches occur before previous breach integrals have completely faded out. However, once the integral threshold has been breached, generating an alarm, embodiments may zero out all previous breach integrals and methods may return to monitor operation 602.

As indicated above, similar methods for employing fadeout to parameter integrals while reducing nuisance alarms may be provided for any number of non-physiological parameters monitored by a ventilatory system. For instance, the method described with reference to FIG. 6 may be appropriately applied to the ventilatory regulation of $FiO_2$ delivery, CO delivery, circuit pressure regulation, PAV support adjustments, occlusion and/or leak detection, infusate delivery, etc.

It will be clear that the systems and methods described herein are well adapted to attain the ends and advantages mentioned as well as those inherent therein. Those skilled in the art will recognize that the methods and systems within this specification may be implemented in many manners and as such is not to be limited by the foregoing exemplified embodiments and examples. In other words, functional elements being performed by a single or multiple components, in various combinations of hardware and software, and individual functions can be distributed among software applications at either the client or server level. In this regard, any number of the features of the different embodiments described herein may be combined into one single embodiment and alternative embodiments having fewer than or more than all of the features herein described are possible.

While various embodiments have been described for purposes of this disclosure, various changes and modifications may be made which are well within the scope of the present invention. Numerous other changes may be made which will readily suggest themselves to those skilled in the art and which are encompassed in the spirit of the disclosure and as defined in the appended claims.

What is claimed is:

1. A method for reducing nuisance alarms while monitoring one or more non-physiological parameters in a ventilatory system, the method comprising:
   receiving alarm conditions, wherein the alarm conditions include a parameter threshold and an integral threshold;
   monitoring at least one parameter of the one or more non-physiological parameters;
   detecting a breach of the parameter threshold;
   calculating an integral of the breach;
   determining whether the integral of the breach is greater than the integral threshold
   detecting an additional breach of the parameter threshold;
   calculating an integral of the additional breach;
   adding an incrementally reduced integral of the breach to the integral of the additional breach; and
   generating an alarm when the incrementally reduced integral of the breach and the integral of the additional breach are greater than the integral threshold.

2. The method of claim 1, further comprising:
   generating an alarm when the integral of the breach is greater than the integral threshold.

3. The method of claim 1, wherein the one or more non-physiological parameters are selected from a group consisting of: $FiO_2$, CO, Percent Support, Pressure Support, circuit pressure, circuit flow, and one or more infusates.

4. The method of claim 1, wherein when the integral of the breach is not greater than the integral threshold, the integral of the breach is incrementally reduced over a predetermined period of time.

5. The method of claim 1, wherein when an alarm is generated, zeroing out the incrementally reduced integral of the breach and the integral of the additional breach.

6. The method of claim 1, wherein the alarm conditions are received via voice activation.

7. A ventilatory system for reducing nuisance alarms while monitoring one or more non-physiological parameters, comprising:
- at least one processor; and
- at least one memory, communicatively coupled to the at least one processor and containing instructions that, when executed by the at least one processor, perform a method comprising:
  - receiving alarm conditions, wherein the alarm conditions include a parameter threshold and an integral threshold;
  - monitoring at least one parameter of the one or more non-physiological parameters;
  - detecting a first breach of the parameter threshold;
  - calculating a first integral of the first breach;
  - determining whether the first integral of the first breach is greater than the integral threshold;
  - when the first integral of the first breach is not greater than the integral threshold, incrementally reducing the first integral of the first breach over a predetermined period of time;
  - detecting a second breach of the parameter threshold;
  - calculating a second integral of the second breach; and
  - determining whether a sum of the incrementally reduced first integral plus the second integral is greater than the integral threshold.

8. The system of claim 7, further comprising:
- generating an alarm when the sum of the incrementally reduced first integral plus the second integral is greater than the integral threshold.

9. The system of claim 8, wherein when an alarm is generated, zeroing out the incrementally reduced first integral and the second integral.

10. The system of claim 7, wherein the one or more non-physiological parameters are selected from a group consisting of: $FiO_2$, CO, Percent Support, Pressure Support, circuit pressure, circuit flow, and one or more infusates.

11. The system of claim 7, wherein alarm conditions are received via voice activation.

* * * * *